(12) United States Patent
Jensen et al.

(10) Patent No.: US 9,078,948 B2
(45) Date of Patent: Jul. 14, 2015

(54) ADHESIVE COMPOSITION

(75) Inventors: Jarl Jensen, Orangeburg, NY (US); Ravi Ramjit, Orangeburg, NY (US); Ta Kang Keng, Orangeburg, NY (US)

(73) Assignee: Euromed Inc., Orangeburg, NY (US)

( * ) Notice: Subject to any disclaimer, the term of this patent is extended or adjusted under 35 U.S.C. 154(b) by 258 days.

(21) Appl. No.: 12/900,603

(22) Filed: Oct. 8, 2010

(65) Prior Publication Data

US 2011/0118363 A1    May 19, 2011

Related U.S. Application Data

(60) Provisional application No. 61/278,587, filed on Oct. 8, 2009, provisional application No. 61/385,043, filed on Sep. 21, 2010.

(51) Int. Cl.
| | | |
|---|---|---|
| *C09J 191/00* | (2006.01) | |
| *A61L 15/58* | (2006.01) | |
| *A61L 15/30* | (2006.01) | |
| *A61L 15/34* | (2006.01) | |
| *A61L 24/04* | (2006.01) | |
| *A61F 5/445* | (2006.01) | |

(52) U.S. Cl.
CPC ............... *A61L 15/58* (2013.01); *A61L 15/30* (2013.01); *A61L 15/34* (2013.01); *A61L 24/043* (2013.01); *A61F 5/445* (2013.01)

(58) Field of Classification Search
CPC ....... A61F 5/445; A61L 15/30; A61L 24/043; A61L 15/58; A61L 15/34
USPC .................................. 514/772.4; 523/111
See application file for complete search history.

(56) References Cited

U.S. PATENT DOCUMENTS

| | | | | |
|---|---|---|---|---|
| 2003/0215413 | A1* | 11/2003 | Fares et al. ............... | 424/70.16 |
| 2004/0241246 | A1* | 12/2004 | Lipman ..................... | 424/486 |
| 2007/0078197 | A1* | 4/2007 | Samuelsen ................ | 523/111 |

* cited by examiner

*Primary Examiner* — Sean Basquill
(74) *Attorney, Agent, or Firm* — Morgan Lewis & Bockius LLP

(57) ABSTRACT

The present invention relates to an adhesive composition applicable to skin comprising: (i) a polar oil or fat including (a) at least one triglyceride and/or (b) at least one fatty acid of the formula R—$CO_2$H, wherein R is a $C_3$ to $C_{30}$ alkyl group; and (ii) at least one homopolymer, and/or copolymer. This invention also relates to a medical adhesive device including such adhesive composition.

4 Claims, 1 Drawing Sheet

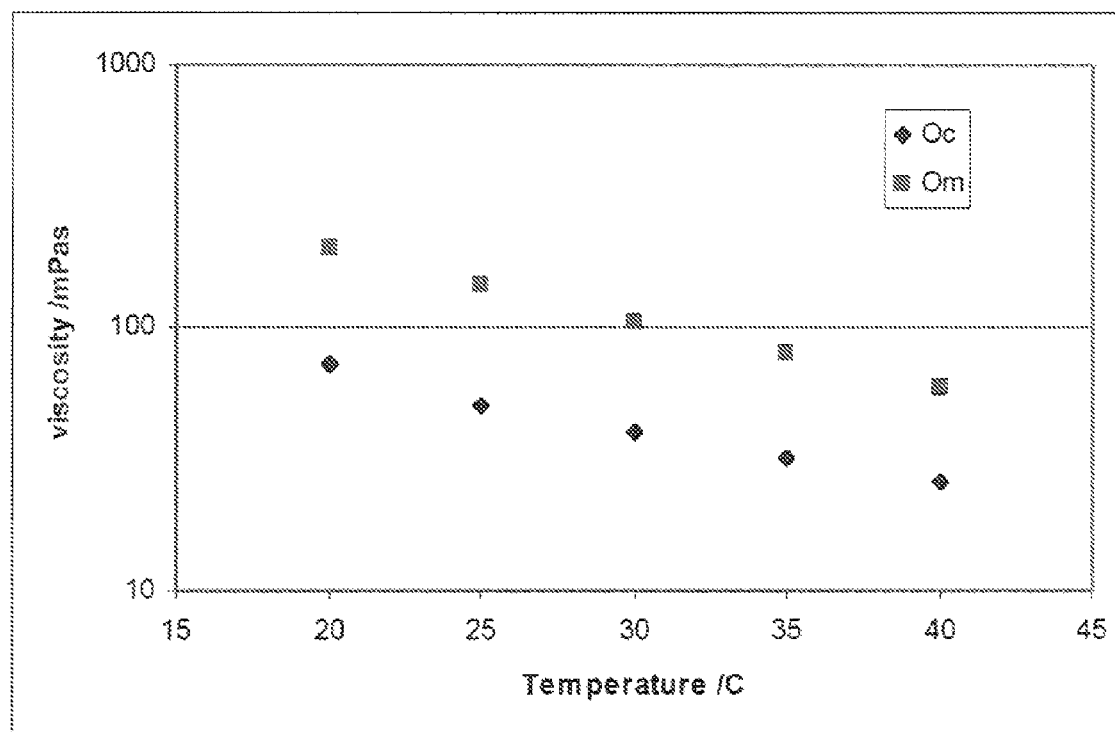

ADHESIVE COMPOSITION

CROSS REFERENCE TO RELATED APPLICATIONS

This application claims priority to and the benefit of U.S. Provisional Patent Application Ser. Nos. 61/278,587 and 61/385,043, filed on Oct. 8, 2009 and Sep. 21, 2010, respectively, the entire disclosures of which are incorporated herein by reference.

TECHNICAL FIELD

The present invention relates to adhesive compositions applicable to skin and their use in a medical adhesive device. The adhesive compositions carry unique features of skin friendliness (e.g. hypoallergenicity), repositionabilty, painless removal, and the ability to initiate natural antimicrobial activities.

BACKGROUND

Conventional adhesive compositions, as well as wound dressings and ostomy products, have been known for many years. Although the industry has been well developed, the current products retain some critical drawbacks. One disadvantage is the inability to reposition the dressing after initial application. Another problem with many conventional adhesive compositions is the pain experienced upon removal. Thus, there remains a strong desire to engineer an adhesive composition, wound dressing, or ostomy product which addresses the conditions above.

Accordingly, one aspect of the invention is to provide an adhesive composition, wound dressing or ostomy product which addresses the need for repositioning after initial application and which reduces the amount of pain a patient experiences upon removal. Other objects of the invention will be apparent from the following description of the invention.

SUMMARY OF THE INVENTION

Broadly stated, the features of the invention are realized, according to one aspect of the invention, by creating an adhesive composition applicable to skin comprising: (i) a polar oil or fat including (a) at least one triglyceride, and/or (b) at least one fatty acid of the formula $R-CO_2H$, wherein R is a $C_3$ to $C_{30}$ alkyl group; and (ii) at least one homopolymer, and/or copolymer. This adhesive composition carries unique features of skin friendliness, e.g. hypoallergenicity, painless removal, repositionability, and the ability to initiate natural antimicrobial activities.

In one embodiment, the present invention relates to a medical adhesive device comprising an adhesive composition comprising: (i) a polar oil or fat including (a) at least one triglyceride, and/or (b) at least one fatty acid of the formula $R-CO_2H$, wherein R is a $C_3$ to $C_{30}$ alkyl group; and (ii) at least one homopolymer, and/or copolymer.

In one embodiment, the present invention relates to a skin fixation or a transdermal drug delivery adhesive matrix composition comprising an adhesive composition comprising: (i) a polar oil or fat including (a) at least one triglyceride, and/or (b) at least one fatty acid of the formula $R-CO_2H$, wherein R is a $C_3$ to $C_{30}$ alkyl group; (ii) at least one homopolymer, and/or copolymer, (iii) at least one tackifier, (iv) at least one hydrophilic fluid-absorbing gum or gel-thickener, and (v) at least one benefit agent.

In another embodiment, the present invention relates to an ostomy adhesive composition comprising: (i) a polar oil or fat including (a) at least one triglyceride and/or (b) at least one fatty acid of the formula $R-CO_2H$, wherein R is a $C_3$ to $C_{30}$ alkyl group; (ii) at least one homopolymer, and/or copolymer, (iii) at least one tackifier, (iv) at least one hydrophilic fluid-absorbing gum or gel-thickener, and (v) at least one benefit agent, wherein the overall triglyceride content is in the range of 1% to 65% by weight of the composition.

DESCRIPTION OF FIGURE

FIG. 1 shows the viscosity vs. temperature profiles of the mineral oil (Om) and coconut oil (Oc). Note that coconut oil melts at 20° C., and below this temperature point there is no measurable flow.

DETAILED DESCRIPTION

The present invention relates to adhesive compositions that can be used in a skin fixation device, wound dressing, and in ostomy fixation.

Pain is sensed when the epidermis of the periwound skin is damaged and/or when the hair is pulled by the adhesive during dressing removal. On wounded skin, over-aggressive adhesive is undesired due to the damage inflicted on the newly grown tissue, and the subsequent delay in healing.

Generally, adhesives can fail in either of three ways: adhesive failure, cohesive failure, or substrate failure. In the case of adhesive failure, the adhesive fails at the adhesive/substrate interface, leaving no residue (e.g. painless removable wound dressing, masking tape); the adhesive has good internal cohesion strength, and relatively weak interfacial strength. Cohesive failure occurs when the adhesive/substrate interfacial force is larger than the adhesive's internal strength, and the adhesive internally breaks during the debonding which leave adhesive residue on the substrate after removal (e.g. pulling chewing gum off hair). Substrate failure occurs when both the adhesive and cohesive strength exceed the substrate's material strength, causing the material to be ripped upon adhesive removal (e.g. waxing body hair).

For skin contact adhesives, adhesive failure is preferred, since cohesive failure generates residue and substrate failure will damage skin and cause pain.

As a benchmark, silicone adhesives are generally considered the gold standard for painless removal. Silicone has low surface energy, and this unique property allows it to "wet" surfaces. Silicone also has low cohesive strength. Therefore, additional chemical crosslinking needs to be introduced as cohesive strength reinforcement. For wound dressings, the adhesive is often formulated to be soft and gentle, which is characterized by the low adhesive storage modulus (G').

This low G' (about 5,000-500,000 Pa) creates an interesting design challenge: the lower the G', the lower the cohesive strength, and more chance for cohesive failure and possibility of leaving a residue. Indeed, many commercial silicone adhesives suffer from this problem. They are designed on the edge of adhesive/cohesive failure limit. The silicone adhesive residues are usually observed at the dressing border, where the shear is maximized.

The low G' gives the silicone adhesive its desired repositionability and painless removal properties. However, it cannot absorb the natural sweat. The silicone contours the skin so well that it forms a non-porous intimate layer on the skin. Silicone adhesive is typically advertised as having a high moisture vapor transmission rate (MVTR), which allows the sweat to evaporate through the adhesive layer. Nevertheless, the passive evaporative sweat management is insufficient. After a day of wearing, irritation of skin and itchiness caused by trapped sweat can be observed. The accumulated sweat promotes bacterial growth and often leads to skin irritation, infection, and possible maceration. Therefore, it is important to incorporate a skin-friendly water absorbent to actively absorb and transport the sweat moisture away from the skin. The hydrocolloid adhesive rightfully accommodates this requirement.

The present hydrocolloid adhesive design approach is directed to obtaining an adhesive G' similar to that of the silicone adhesive in order to achieve the desired repositionability and painless removal design attributes. The adhesive can incorporate triglycerides to achieve this goal.

Typically, triglycerides are purposely excluded from adhesive formulations due to their oxidation rancid potential and bio-degrading vulnerability. However, by carefully selecting a highly saturated or artificially hydrogenated triglyceride, the adverse effects of rancidity can be avoided or eliminated. In the case of wound care and ostomy care, it is often unavoidable to leave a trace amount of adhesive residue on the skin or in the wound bed. Therefore, bio-degradable oil is more desired and provides unexpected advantages in adhesive formulations compared to biologically inert synthetic oils such as mineral oil.

In this patent application, it is demonstrated that triglycerides, such as those predominant in coconut and/or vegetable oils, have the ability to entirely or partially replace synthetic oils in general skin adhesive, wound dressing, and ostomy applications. In addition, it is also demonstrated that triglycerides can be incorporated as a highly temperature sensitive adhesive, and the adhesion is skin temperature activated.

Such skin friendly adhesives, containing high triglyceride content can be designed to incorporate lipid-soluble benefit agents for transdermal delivery applications. For hydrophilic-based benefit agents, emulsifiers can be incorporated to aid the suspension of benefit agents within the triglyceride-based adhesive matrix.

In one embodiment, the present invention embraces an adhesive composition applicable to skin comprising: (i) a polar oil or fat including (a) at least one triglyceride and/or (b) at least one fatty acid of the formula R—$CO_2$H, wherein R is a $C_3$ to $C_{30}$ alkyl group; and (ii) at least one homopolymer, and/or copolymer.

In one embodiment, the present invention embraces an adhesive composition applicable to skin comprising: (i) a polar oil or fat including (a) at least one triglyceride and/or (b) at least one fatty acid of the formula R—$CO_2$H, wherein R is a $C_3$ to $C_{30}$ alkyl group; and (ii) at least one homopolymer, and/or copolymer, wherein the fatty acid is derived from a highly saturated vegetable oil.

In one embodiment, the present invention embraces an adhesive composition applicable to skin comprising: (i) a polar oil or fat including (a) at least one triglyceride and/or (b) at least one fatty acid of the formula R—$CO_2$H, wherein R is a $C_3$ to $C_{30}$ alkyl group; and (ii) at least one homopolymer, and/or copolymer, wherein the vegetable oil is coconut oil.

In one embodiment, the present invention embraces an adhesive composition applicable to skin comprising: (i) a polar oil or fat including (a) at least one triglyceride and/or (b) at least one fatty acid of the formula R—$CO_2$H, wherein R is a $C_3$ to $C_{30}$ alkyl group; and (ii) at least one homopolymer, and/or copolymer, wherein the vegetable oil is obtained from a further modified, refined, virgin, fractionated, or hydrogenate source.

In one embodiment, the present invention embraces an adhesive composition applicable to skin comprising: (i) a polar oil or fat including (a) at least one triglyceride and/or (b) at least one fatty acid of the formula R—$CO_2$H, wherein R is a $C_3$ to $C_{30}$ alkyl group; (ii) at least one homopolymer, and/or copolymer, and (iii) a tackifier.

In one embodiment, the present invention embraces an adhesive composition applicable to skin comprising: (i) a polar oil or fat including (a) at least one triglyceride and/or (b) at least one fatty acid of the formula R—$CO_2$H, wherein R is a $C_3$ to $C_{30}$ alkyl group (ii) at least one homopolymer, and/or copolymer, and (iii) a tackifier selected from the group consisting of natural rosin, modified rosin, glycerol ester of natural rosin, glycerol ester of modified rosin, pentaerythritol ester of natural rosin, pentaerythritol ester of modified rosin, phenolic-modified terpene resin, aliphatic petroleum hydrocarbon resin, and cycloaliphatic resin.

In one embodiment, the present invention embraces an adhesive composition applicable to skin comprising: (i) a polar oil or fat including (a) at least one triglyceride and/or (b) at least one fatty acid of the formula R—$CO_2$H, wherein R is a $C_3$ to $C_{30}$ alkyl group; and (ii) at least one homopolymer, and/or copolymer, and (iii) a synthetic oil.

In one embodiment, the present invention embraces an adhesive composition applicable to skin comprising: (i) a polar oil or fat including (a) at least one triglyceride and/or (b) at least one fatty acid of the formula R—$CO_2$H, wherein R is a $C_3$ to $C_{30}$ alkyl group; and (ii) at least one homopolymer, and/or copolymer, and (iii) a mineral oil or silicone oil.

In one embodiment, the present invention embraces an adhesive composition applicable to skin comprising: (i) a polar oil or fat including (a) at least one triglyceride and/or (b) at least one fatty acid of the formula R—$CO_2$H, wherein R is a $C_3$ to $C_{30}$ alkyl group; and (ii) at least one homopolymer, and/or copolymer, wherein the copolymer comprises at least two immiscible monomers.

In one embodiment, the present invention embraces an adhesive composition applicable to skin comprising: (i) a polar oil or fat including (a) at least one triglyceride and/or (b) at least one fatty acid of the formula R—$CO_2$H, wherein R is a $C_3$ to $C_{30}$ alkyl group; (ii) at least one homopolymer, and/or copolymer, and (iii) a hydrophilic fluid-absorbing gum or gel-thickener, wherein the gum or gel-thickener is cationic, anionic, or non-ionic.

In one embodiment, the present invention embraces an adhesive composition applicable to skin comprising: (i) a polar oil or fat including (a) at least one triglyceride and/or (b) at least one fatty acid of the formula R—$CO_2$H, wherein R is a $C_3$ to $C_{30}$ alkyl group; (ii) at least one homopolymer, and/or copolymer, and (iii) a hydrophilic fluid-absorbing gum or gel-thickener, wherein the gel-thickener is a water soluble or swellable hydrocolloid or a mixture therein.

In one embodiment, the present invention embraces an adhesive composition applicable to skin comprising: (i) a polar oil or fat including (a) at least one triglyceride and/or (b) at least one fatty acid of the formula R—$CO_2$H, wherein R is a $C_3$ to $C_{30}$ alkyl group; (ii) at least one homopolymer, and/or copolymer, and (iii) a hydrophilic fluid-absorbing gum or gel-thickener, wherein the gel-thickener is selected from a group consisting of carboxymethylcellulose, hydroxyethylcellulose (HEC), hydroxypropylcellulose (HPC), pectin, carragean, and gelatin.

In one embodiment, the present invention embraces a medical adhesive device comprising an adhesive composition including: (i) a polar oil or fat including (a) at least one triglyceride and/or (b) at least one fatty acid of the formula R—$CO_2$H, wherein R is a $C_3$ to $C_{30}$ alkyl group; and (ii) at least one homopolymer, and/or copolymer.

In one embodiment, the present invention embraces a medical adhesive device comprising an adhesive composition including: (i) a polar oil or fat including (a) at least one triglyceride and/or (b) at least one fatty acid of the formula R—$CO_2$H, wherein R is a $C_3$ to $C_{30}$ alkyl group; (ii) at least one homopolymer, and/or copolymer; and (iii) a tackifier.

In one embodiment, the present invention embraces a medical adhesive device comprising an adhesive composition comprising: (i) a polar oil or fat including (a) at least one triglyceride and/or (b) at least one fatty acid of the formula R—$CO_2$H, wherein R is a $C_3$ to $C_{30}$ alkyl group; (ii) at least one homopolymer, and/or copolymer; and (iii) a tackifier selected from the group consisting of natural rosin, modified rosin, glycerol ester of natural rosin, glycerol ester of modified rosin, pentaerythritol ester of natural rosin, pentaerythritol ester of modified rosin, phenolic-modified terpene resin, aliphatic petroleum hydrocarbon resin, and cycloaliphatic resin.

In one embodiment, the present invention embraces a medical adhesive device comprising an adhesive composition including: (i) a polar oil or fat including (a) at least one triglyceride and/or (b) at least one fatty acid of the formula R—$CO_2$H, wherein R is a $C_3$ to $C_{30}$ alkyl group; (ii) at least one homopolymer, and/or copolymer; and (iii) a tackifier; and (iv) a synthetic oil.

In one embodiment, the present invention embraces a medical adhesive device comprising an adhesive composition comprising: (i) a polar oil or fat including (a) at least one triglyceride and/or (b) at least one fatty acid of the formula R—$CO_2$H, wherein R is a $C_3$ to $C_{30}$ alkyl group; (ii) at least one homopolymer, and/or copolymer; and (iii) a tackifier; and (iv) a synthetic oil, wherein the synthetic oil is mineral oil or silicone oil.

In one embodiment, the present invention embraces a medical adhesive device comprising an adhesive composition including: (i) a polar oil or fat including (a) at least one triglyceride and/or (b) at least one fatty acid of the formula R—$CO_2$H, wherein R is a $C_3$ to $C_{30}$ alkyl group; and (ii) at least one homopolymer, and/or copolymer, wherein the copolymer comprises at least two immiscible monomers.

In one embodiment, the present invention embraces a medical adhesive device comprising an adhesive composition including: (i) a polar oil or fat including (a) at least one triglyceride and/or (b) at least one fatty acid of the formula R—$CO_2$H, wherein R is a $C_3$ to $C_{30}$ alkyl group; (ii) at least one homopolymer, and/or copolymer, and (iii) a hydrophilic fluid-absorbing gum or gel-thickener, wherein the copolymer comprises at least two immiscible monomers.

In one embodiment, the present invention embraces a medical adhesive device comprising an adhesive composition including: (i) a polar oil or fat including (a) at least one triglyceride and/or (b) at least one fatty acid of the formula R—$CO_2$H, wherein R is a $C_3$ to $C_{30}$ alkyl group; (ii) at least one homopolymer, and/or copolymer, and (iii) a hydrophilic fluid-absorbing gum or gel-thickener, wherein the copolymer comprises at least two immiscible monomers, and wherein the gel-thickener is a water soluble or swellable hydrocolloid or a mixture therein.

In one embodiment, the present invention embraces a skin fixation or a transdermal drug delivery adhesive matrix composition comprising an adhesive composition including: (i) a polar oil or fat including (a) at least one triglyceride and/or (b) at least one fatty acid of the formula R—$CO_2$H, wherein R is a $C_3$ to $C_{30}$ alkyl group; (ii) at least one homopolymer, and/or copolymer, (iii) at least one tackifier, (iv) at least one hydrophilic fluid-absorbing gum or gel-thickener, and (v) at least one benefit agent.

In one embodiment, the present invention embraces an ostomy adhesive composition comprising: (i) a polar oil or fat including (a) at least one triglyceride and/or (b) at least one fatty acid of the formula R—$CO_2$H, wherein R is a $C_3$ to $C_{30}$ alkyl group; (ii) at least one homopolymer, and/or copolymer, (iii) at least one tackifier, (iv) at least one hydrophilic fluid-absorbing gum or gel-thickener, and (v) at least one benefit agent, wherein the overall triglyceride content is in the range of 1% to 25% by weight of the composition.

In one embodiment, the homopolymer is a homopolymer rubber. Examples of homopolymer rubber include, but are not limited to, isobutylene, epichlorhydrin rubber, chloroprene rubber, isoprene rubber, bromobutyl rubber, and chlorobutyal rubber.

Suitable copolymer contains at least two monomers which have very different glass transition temperatures so that they are immiscible in each other and phase separate at room temperature. Examples of such copolymers include, but are not limited to, styrene isoprene styrene (SIS), styrene butadiene styrene (SBS), styrene ethylene-butylene styrene (SEBS), styrene-ethylene-styrene (SES), styrene-propylene-styrene (SPS), and ethylene vinyl acetate (EVA). Preferably, the copolymer is selected from the group consisting of Kraton™ D 1107 (Shell Chemicals), Kraton™ D 1100, Kraton™ D1102, Kraton™ 4000, Kraton™ G1600, Kraton™ G4600 and mixtures thereof. More preferably, the copolymer is an SIS polymer such as Kraton™ D1107 (Shell Chemicals).

In one embodiment, the copolymer is SIS. SIS can form the base polymer that acts as the foundation to build the adhesive. The styrene and the isoprene have very different glass transition temperatures (Tg) (+100° C. and −60° C. respectfully). They are immiscible and phase separate at room temperature: the styrene crystallizes, while the isoprene remains as a liquid. Since SIS has styrene on both ends of the isoprene chains, the hardened styrene crystals act as nanoscopic physical cross-linkers and provide integrity to the adhesive, which gives the adhesive mix its cohesive strength. Isoprene, on the other hand, has low Tg, and its Tg has to be modified by means of additional tackifier. In addition, the G' of the adhesive can be modified by addition of plasticizer, often oil or fat. Depending on the chemistry of the chosen oil and the tackifier, they can have various degrees of affinity toward styrene and isoprene. In general, most oils and tackifiers chosen have to have good affinity to the mid-block isoprene domain (I), and moderate to no affinity to the end-block styrene domains (S) to preserve cohesive strength.

Suitable tackifiers often have low molecular weight with higher Tg than the isoprene. Examples of suitable tackifiers include, but are not limited to, natural rosin, modified rosin, glycerol ester of natural rosin, glycerol ester of modified rosin, pentaerythritol ester of natural rosin, pentaerythritol ester of modified rosin, phenolic-modified terpene resin, aliphatic petroleum hydrocarbon resin, and cycloaliphatic resin.

The oil (O) comes from either the natural plant or animal (triglycerides), or from petroleum (mineral oil). Typically, natural triglyceride-based oil is not used in adhesive due to its vulnerability to oxidation, which turns the oil rancid. To address the adverse rancidity effect, the inventors use a native, highly saturated coconut oil (Oc). The Oc has high saturated oil content of 92%, which therefore provides longer shelf stability even without hydrogenation. Typically, Oc stays fresh for at least 2 years without the need for a nitrogen blanket or any other oxygen eliminating packaging. Hydrogenated Oc and/or an antioxidant can also be used to minimize or eliminate the rancidity process for even longer shelf life. The oil provides a means to dilute the isoprene domain and thus lower the adhesive's storage modulus (G'). The low G' allows the adhesive to conform to the surface in reduced time.

The coconut oil has much lower viscosity than mineral oil (Om). To study the effect of the oil in the adhesive, a series of experiments was performed by mixing fixed amounts of base polymer (K) with various amounts of oil until the maximum tack is reached. The tackiness of the O/K mix is felt between the fingers for each mixing ratio. The tacky sensation test is a quick qualitative comparison. Although not quantitative, it does provide extremely useful insight into the tack effectiveness of oil. The results are tabulated below.

For Om/K mix, the maximum tack on skin was felt at a ratio of 8/1 (wt./wt.) with the tack score of 2/5. (A tack score of 5/5 is considered as a mark for the current SureSkin II Euromed hydrocolloid, and a tack score of 0/5 is considered as no tack.) The tack score is similar at body temperature and room temperature. The Om/K mix is a rubbery oil gel that has good cold flow resistance but poor tack. When the gel is left at room temperature (i.e., about 25° C.) for about eight hours, the gel does not deform or change shape.

For the Oc/K mix, the tack is much higher compared to an Om/K mix. The maximum tack occurs at a weight/weight ratio of 1.6/1, with a tack score of 5/5 at body temperature. The Oc/K mix has a very unique property in that it is very stiff and hard at room temperature, and turns into a very soft and tacky oil gel at body temperature. The tack score at room temperature is mere 1/5. This extreme temperature dependency is due to the unique melting property of the coconut oil: the coconut oil melts at 20° C.

|  | Ratio (wt./wt.) | Tack (x/5) room temp (25° C.) | Tack (x/5) skin temp (33° C.) |
| --- | --- | --- | --- |
| Om/K | 8 | 2 | 2 |
| Oc/K | 1.6 | 1 | 5 |

The high temperature dependency provides a very useful benefit: namely, the adhesive is body heat activated. The adhesive does not stick well at room temperature. This allows the dressing to be handled and repositioned during the initial dressing application. As the dressing is set in place, the body heat slowly melts the oil, the adhesive quickly conforms to the skin within 10 minutes, and a strong bond rapidly builds.

Comparing the Om vs. Oc, either oil can be incorporated to reduce the adhesive G'. However, Oc has a much higher bonding capability to skin at skin temperature. Although oils are generally not considered as tackifiers to provide tack, the Oc's high bonding capacity allows a tacky adhesive gel to be made even without the use of a tackifier. This can be explained by the rheological measurements: the Oc broadens and reduces the styrene domain's Tg peak. The Oc has higher affinity toward the styrene domain compared to that of mineral oil. Consequently, the Oc weakens the styrene domain, allowing the adhesive to lose some of its cohesive strength and transforming the mixture into an adhesive without the need for tackifier. The Oc only expresses this behavior above the Oc melting temperature (20° C.), forming a temperature sensitive adhesive. The inventors have therefore formulated a skin friendly adhesive with Oc based on an acquired understanding of the characteristics Oc.

The present adhesive compositions comprise fluid absorbent materials which are classified as hydrocolloids (HC). Hydrocolloids are used in skin fixation devices, wound dressings, transdermal patches, and in ostomy applications. In skin fixation and wound dressing applications, the hydrocolloid adhesive mix is laminated to a polymer film to form an adhesive laminate. This laminate can be applied to intact skin (skin fixation) or wounds (wound dressing), acting as an environmental barrier and a wound cushion, and taking up excess body sweat and wound exudate. In ostomy fixation system, pure hydrocolloid adhesive is pressed into a ring shape and is used to bind the ostomy pouch onto the skin. In addition, the adhesive can be used as a protective barrier or sealant around the stoma to block the effluent from contacting penstoma skin.

The present compositions can be applied to medical fixation, such as IV dressing, adhesive foam, and bordered foam dressings. Such medical fixation will carry the features of painless removal and avoidance of damage to periwound skin. The IV dressing is a transparent/translucent thin dressing that acts as a skin barrier to cover the IV injection port. The adhesive foam is a foam dressing with an adhesive coating on the skin contact side. The adhesive allows the foam to adhere and provides a gentle bond to the wound site without the need for a nurse to apply secondary adhesive to frame the foam border. The bordered foam dressing has the adhesive border pre-laminated to the foam, and the dressing is used as is, without the need for secondary adhesive.

Suitable hydrophilic fluid-absorbing gum or gel-thickener serves the dual purpose of taking up moisture and providing extra cohesive strength for the adhesive composition. The suitable hydrophilic fluid-absorbing gum or gel-thickener provides gentle tack, and not fluid absorption.

The skin fixation adhesive was formulated via experimental design. The protocol begins with the fixed amount base SIS co-polymer, and then tackifier and oil are iteratively added to form the continuous phase. The adhesive performance is tested to have the desired tack and form the adhesive base. After the adhesive continuous phase is formulated, the solid discontinuous phase or the fluid absorbing material, (e.g., carboxymethyl cellulose gum (CMC)), is added. Depending on the amount of CMC added, the continuous phase formulation may or may not need to be modified.

CMC is a modified salt of cellulose. The CMC serves the dual purpose of taking up moisture and providing extra cohesive strength for the adhesive mix. The water absorption capacity is dependent on the concentration of the CMC added. Other water absorbing material or gum can also be added jointly to achieve a synergetic water absorbing effect.

As used herein, the term "derived from" is defined as "obtained from highly saturated vegetable oils by known mechanical or chemical purification, separation, or extraction techniques." By way of example, in one embodiment of the invention, this term is used where fatty acid is derived from a highly saturated vegetable oil, As used herein, the term "obtained from" is defined as "generated or synthesized from these designated sources by known purification, separation, or extraction techniques." By way of example, in one embodiment of the invention, this term is used where the vegetable oil is obtained from a further modified, refined, virgin, fractionated, or hydrogenated source, As used herein, the term "benefit agent" includes any active ingredient that is to be delivered into and/or onto the skin, hair or nail at a desired location, such as a cosmetic agent or a pharmaceutical agent.

By "cosmetic agent", it is meant any ingredient that is appropriate for cosmetically treating, providing nutrients to, and/or conditioning, e.g., the hair, nail, and/or skin via topical application. By "pharmaceutical agent," it is meant any drug that is either hydrophobic or hydrophilic in nature and appropriate for topical use.

Examples of suitable benefit agents include, but are not limited to, analgesics, anti-inflammatory agents, both of steroidal and non-steroidal nature, antihistamines, antipruritics, general and local anesthetics, vasoconstrictors, antihypertensives including vasodilators, diuretics and ACE inhibitors, cardiac agents, hemostatics and styptics, mucolytics, antitussives, expectorants, mucoprotectants, antineoplastics, immunologic agents, antibiotics, antivirals, antidiabetics, bronchodilators, sympathomimetics, adrenergics, adrenergic blockers, anticholinergics, antimuscarinics, antispasmodics, skeletal muscle relaxants, uterine and antimigraine drugs, sedatives, hypnotics, anxiolytics, central nervous system stimulants, antidepressants and other psychopharmaceutical agents, antiepileptics, antiemetics and hormones.

Analgesics include, but are not limited to, opiate and non-opiate analgesics and antagonists of both synthetic and natural origin. Examples include, but are not limited to, morphine derivatives, codeine derivatives, methadone, propoxyphene, meperidine, fentanyl, morphinans such as levorphanol, and pentazocine. Other analgesics include, but are not limited to, acetaminophen.

Some examples of non-steroidal anti-inflammatory agents include, but are not limited to, propionic acids such as fenoprofen, ibuprofen, ketoprofen; fenamates such as meclofenamate and mefenamic acid; acetic acids such as diclofenac, etodolac, indomethacin, sulindac; oxicams such as piroxicam; and other agents such as nabumetone, and oxyphenbutazone. Additionally, the following agents are also known as analgesic/anti-inflammatory agents: salicylates such as aspirin, methyl salicylate; monoglycol salicylate; salsalate; gold compounds such as auranofin; allopurinol, colchicine, and methysergide.

Examples of steroidal anti-inflammatory agents include, but are not limited to, hydrocortisone, prednisolone, dexamethasone, triamcinolone, fluocinolone, methylprednisolone, betamethasone, flumetasone, fluorometholone, beclomethasone and fluocinonide.

Antihistamines can be of $H_1$ or $H_2$ antagonists or other types of histamine release inhibitors. The $H_1$ antagonists can be sedating or non-sedating. Examples of $H_1$-sedating antihistamines include, but are not limited to, diphenhydramine, chlorpheniramine, tripelennamine, promethazine, clemastine and doxylamine. Examples of $H_1$-non-sedating antihistamines include, but are not limited to, astemizole, terfenadine and loratadine. Examples of $H_2$ antagonists include, but are not limited to, cimetadine, famotidine, nizatidine, and ranitidine. An example of a histamine-release-inhibitor is cromolyn.

Examples of local anesthetics include, but are not limited to, dibucaine, lidocaine, benzocaine, p-butylaminobenzoic acid-2-(diethylamino) ethyl ester, procaine, tetracaine, chloroprocaine, oxyprocaine, mepivacaine, bupivacaine, cocaine, piperocaine, dyclonine, etc.

Examples of vasoconstrictors include, but are not limited to, naphazoline, tetrahydrozoline, oxymetazoline and phenylephrine.

Examples of hemostatics and styptics include, but are not limited to, thrombin, phytonadione, protamine, aminocaproic acid, tranexamic acid, rutin, hesperidin, silver salts, and ferric salts.

Examples of antibacterials include, but are not limited to, sulfa drugs, penicillins, cephalosporins, tetracyclines, erythromycins, aminoglycosides, polypeptide antibiotics, fluoroquinolones, chloramphenicol, clindamycin, rifampin, spectinomycin, vancomycin, bacitracin, cyclosporine, dapsone, ethambutol, ethionamide, isoniazid, nitrofurantoin, pyrazinamide, and trimethoprim. Additional agents include antimalarials, amebicides, antiprotozoals, anthelmintics, pediculicides and scabicides.

Examples of antiviral drugs include, but are not limited to, viral DNA polymerase inhibitors such as foscarnet, protease inhibitors, thymidine kinase inhibitors, sugar or glycoprotein synthesis inhibitors, structural protein synthesis inhibitors, attachment and adsorption inhibitors, amantadine, and nucleoside analogues such as acyclovir, didanosine, ganciclovir, idoxuridine, ribavarin, trifluridine, vidarabine, zalcitabine, zidovudine, etc. acyclovir, penciclovir, valacyclovir, and ganciclovir.

Examples of mucolytics include, but are not limited to, potassium iodide, sodium thiocyanate, urea, guanidine hydrochloride, N-acetylcysteine, dithiotheritol, and proteolytic enzymes such as chymotrypsin and trypsin. These agents can be used to affect mucus production and the elasticity and viscosity of the mucus produced.

Examples of hormones include, but are not limited to, insulin, LHRH, growth hormone, calcitonin, thyroid hormones, and male and female hormones such as testosterones, estrogens and progesterones.

Examples of astringents include, but are not limited to, aluminum salts such as alum, aluminum acetate, aluminum chloride, aluminum chlorohydrates, aluminum sulfate, aluminum zirconium chlorohydrate, bismuth subcarbonate, bismuth subnitrate, calamine, glutaral, methenamine, potassium permanganate, resorcinol, silver nitrate, tannic acid, zinc caprylate, zinc chloride, zinc oxide, zinc pyrithione, zinc sulfate and zinc undecylenate.

Some examples of irritants, rubifacients, and vesicants include, but are not limited to, anthralin, benzoin tincture, camphor, cantharidin, capsicum, coal tar, ichthammol, juniper tar, menthol, balsams such as Peruvian balsam and Tolu balsam.

Topical antifungals include, but are not limited to, haloprogin, ciclopirox, flucytosine, miconazole, econazole, clotrimazole, fluconazole, oxiconazole, sulconazole, metronidazole, itraconazole, ketoconazole, butaconazole, terconazole, nystatin, povidone-iodine, tolnaftate, benzoic acid, salicylic acid, mercuric oxide, resorcinol, triacetin, undecylenic acid and its calcium, copper and zinc salts.

Topical anesthetics include, but are not limited to, the local anesthetics described above and benzyl alcohol, camphor, camphorated metacresol, juniper tar, menthol, phenol, phenolate sodium, resorcinol, methyl salicylate, turpentine oil, camphor, menthol, methyl nicotinate, capasaicin, capsicum containing capsaicin, and capsicum oleoresin containing capsaicin.

Examples of keratolytics and cauterizing agents include, but are not limited to, salicylic acid, podophyllum resin, podolifox, cantharidin, the chloroacetic acids and silver nitrate.

Examples of topical bactericides and disinfectants include, but are not limited to, thimerosal, phenol, thymol, benzalkonium chloride, benzethonium chloride, chlorhexidine, povidone iodine, cetylpyridinium chloride, eugenol, trimethylammonium bromide, etc.

Short-chain fatty acids (SCFA) are fatty acids with aliphatic tails of fewer than six carbons. Short chain fatty acids useful in the practice of the present invention include, but are not limited to acetic acid, propionic acid, isobutyric acid (2-methylpropanoic acid), butyric acid, isovaleric acid (3-methylbutanoic acid), valeric acid (pentanoic acid), caproic acid (hexanoic acid).

Medium-chain fatty acids (MCFA) are fatty acids with aliphatic tails of 6-12. Medium chain fatty acids useful in the practice of the present invention include, but are not limited to, caproic acid (C6), caprylic acid (C8), capric acid (C10) and lauric acid (C12). In an embodiment of the invention, coconut oil which is a blend of 2(C6):55(C8):42(C10):1 (C12) is a preferred source of fatty acids.

Long-chain fatty acids (LCFA) are fatty acids with aliphatic tails longer than 12 carbons. Long chain fatty acids useful in the practice of the present invention include, but are not limited to, myristic acid (14 carbons), palmitic acid (16 carbons), oleic acid (18 carbons—monounsaturated), stearic acid (18 carbons—saturated) and erucic acid (22 carbons). In one embodiment of the invention, myristic acid and palmitic acid are preferred long-chain fatty acids.

Very-Long-chain fatty acids (VLCFA) are fatty acids with aliphatic tails longer than 22 carbons. Very-Long-chain fatty acids are useful in the practice of the present invention.

Essential Fatty Acids useful in the practice of the present invention include, but are not limited to, alpha linolenic acid, eicosapentaenoic acid, docosahexaenoic acid, and gamma linolenic acid. In an embodiment of the invention, alpha linolenic acid and eicosapentaenoic acid are preferred.

Hydrocolloids are known in the wound care art. Hydrocolloids useful in the practice of the present invention include, but are not limited to, water absorbing and/or water swellable material such as carboxymethylcellulose, pectin, gelatin, high molecular weight carbowax, carboxypolymethylene, carboxymethyl starches, alginates, carrageenan, gelatine, citrus pectin, powdered pectin, synthetic or natural gums, such as gum guar, gum arabic, locust bean gum, karaya and mixtures thereof.

In an embodiment of the invention, the wound dressing may contain elastomeric binders and tackifiers.

Elastomeric binders useful in the practice of the present invention include, but are not limited to, diblock, triblock, or multiblock elastomeric copolymers such as olefinic copolymers such as styrene-isoprene-styrene, styrene-butadiene-styrene, styrene-ethylene/butylene-styrene, or styrene-ethylene/propylene-styrene, such as those available from the Shell Chemical Company, under the trade designation KRATON® elastomeric resin; polyurethanes, such as those available from E. I. Du Pont de Nemours Co., under the trade name LYCRA® polyurethane; polyamides, such as polyether block amides available from Ato Chemical Company, under the trade name PEBAX® polyether block amide; or polyesters, such as those available from E. I. Du Pont de Nemours Co., under the trade name HYTREL® polyester; natural rubbers, silicone rubber, polyisobutylene rubber, and acrylonitrile rubber. In an exemplary embodiment, the KRATON® olefinic copolymers are preferred.

Tackifiers include, but are not limited to, pine derived rosins (gum rosin, wood rosin, tall oil rosin) and hydrogenated rosins, hydrocarbons and hydrogenated hydrocarbon resins such as C5 aliphatic resins, C9 aromatic resins, and C5/C9 aliphatic/aromatic resins; pure monomers, hydrogenated pure monomers, and water based dispersions. Representative tackifiers, known by their tradenames are FORAL® 85 and ARKON®P115. FORAL® 85 is a hydrocarbon tackifier. ARKON® P115 is a hydrogenated hydrocarbon tackifier. In an embodiment of the invention, FORAL® 85 and ARKON®P115 are preferred.

The Manufacture of the Wound Dressing of the Present Invention

The wound dressing of the present invention is prepared by blending the ingredients according to methods known to those skilled in the art.

For example, in an embodiment of the invention, the wound dressing is prepared by simply blending fatty acids (obtained from, e.g., coconut oil) and hydrocolloids.

In another embodiment of the invention, the wound dressing is prepared by blending fatty acids, hydrocolloids, and elastomers.

In a further embodiment of the invention, the wound dressing of the present invention is prepared by blending fatty acids, hydrocolloids, elastomers and tackifiers. In an embodiment of the invention, the elastomer is first blended with the fatty acid(s); then the other components are added.

In yet another embodiment, mixtures of fatty acids may be used. For example, medium chain fatty acids, essential fatty acids, and long chain fatty acids may be blended in a 1:1:1 ratio to create a mixture of fatty acids. Also, the ratio of each fatty acid in the mixture can be adjusted, with a particular fatty acid being the dominant fatty acid desired by the formulator. In other words, a mixture of medium chain, essential and long chain fatty acids may be blended, wherein the essential fatty acid is the dominant fatty acid. Also, the mixture of fatty acids may be composed of simply two fatty acids, such as an essential fatty acid and a long chain fatty acid mixture. A medium chain fatty acid and a long chain fatty acid mixture is also feasible. The ratios of these two fatty acids may be 1:1 or one fatty acid may be dominant. Further, mixtures of one kind of fatty acid may be used. For example, a mixture of essential fatty acids such as alpha linolenic and eicosapentanoic acid may be used; said fatty acids may be in equal parts, or one may dominate. A mixture of long chain fatty acids, such as myristic acid, erucic acid, and stearic acid, is feasible, and said acids may be in equal parts, or one may dominate.

Additionally, a blend of many fatty acids may be prepared. For example, in an embodiment of the invention, a fatty acid blend comprised of alpha linolenic, coconut oil, erucic acid, myristic acid and eicosapentanoic acid may be used in the wound dressings of the present invention. If desired, said fatty acids may be in equal proportions or one or several fatty acids may dominate. For example, alpha linolenic acid and coconut oil may predominate.

Certain aspects of the invention can be understood in greater detail from the following examples.

Example: Skin Fixation Formulation

| Ingredient | % by wt. |
|---|---|
| Kraton D1161, SIS | 26 |
| Oc | 29 |
| Wingtack ® 10, Cray Valley | 13 |
| Oppanol ® B12, PIB | 16 |
| CMC | 16 |

To achieve the low G', and painless removal, a liquid tackifier Wingtack 10 with low Tg is used. In addition polyisobutylene Oppanol B12 (polyisobutylene, PIB) is used to provide good skin wetability. The CMC provides the water absorption capability. The Oc provides the low G', the skin friendliness, and allows heat activation of the adhesive. The SIS provides cohesion and serves as the foundation for the adhesive.

This adhesive provides a high tack 5/5, repositionability, almost painless removal, and leaves no residue.

Example: Ostomy Formulation

| Ingredient | % by wt. |
| --- | --- |
| Kraton D1161 SIS | 6 |
| Oc | 5 |
| Oppanol ® B12, PIB, BASF | 52 |
| Pectin | 25 |
| CMC | 12 |

PIB provides the main foundation of the moldable adhesive. SIS provides the cohesive strength. Oc serves as a plasticizer and skin friendly moisturizing agent. Pectin and CMC absorb the water and provide the balanced pH.

This adhesive is fully moldable, leaves no residue, and can be painlessly removed. Since no tackifier used, it does not leave a residue on hand during the molding or application process.

Comparison of Ingredient's Qualitative Properties in the Adhesive Performance

| Ingredient | G' | Adhesion |
| --- | --- | --- |
| SIS | + | − |
| Om | − | / |
| Oc | − | + |
| tackifier | − | + |
| water absorbent | + | − |

+: positive contribution
−: negative contribution
/: no significant contribution The following non limiting exemplary formulations illustrate the practice of the present invention:

Example XX

| Ingredients | EXAMPLE | | | |
| --- | --- | --- | --- | --- |
| | XX.1 wt., grams | XX.2 wt., grams | XX.3 wt., grams | XX.4 wt., grams |
| Vector 4230 ® SIS radial copolymer Dow/Exxon Mobil | 100 | 100 | 100 | 100 |
| $O_M$ | 100 | 100 | 100 | 100 |
| $O_C$ | 0 | 0 | 20 | 30 |
| Arakon P90 Arakawa | 200 | 250 | 250 | 250 |
| Performance | | | | |
| Tack (x/5) | 2 | 4 | 4 | 5 |

EXAMPLE XX demonstrates the affect coconut oil has on the adhesive without the interference of CMC
EXAMPLE X (Oc/K=1.6)
a. 62% weight coconut oil
b. 38% weight Kraton 1161
EXAMPLE 1 is a representative composition of one aspect of the present invention.
a. 30 weight % coconut oil,
b. 25 weight % carboxymethylcellulose
c. 30 weight % elastomer (KRATON®) 1161
d. 15 weight % tackifier (ARKON®P115)

EXAMPLE 2 is a representative composition of one aspect of the present invention.
a. 6.0 weight % coconut oil
b. 36 weight % carboxymethylcellulose
c. 18 weight % elastomer (KRATON®) 1161
d. 40 weight % tackifier (FORAL®85)
EXAMPLE 3 is a representative composition of one aspect of the present invention.
a. 50 weight % coconut oil
b. 50 weight % carboxymethylcellulose
EXAMPLE 4 is a representative composition of one aspect of the present invention.
a. 30.0 weight % alpha linolenic acid
b. 25 weight % carboxymethylcellulose
c. 30 weight % elastomer (KRATON®)
d. 15 weight % tackifier (FORAL® 85)
EXAMPLE 5 is a representative composition of one aspect of the present invention.
a. 6.0 weight % myristic acid
b. 36 weight % carboxymethylcellulose
c. 18 weight % elastomer (KRATON®)
d. 40 weight % tackifier (FORAL®85)
EXAMPLE 6 is a representative composition of one aspect of the present invention.
a. 30.0 weight % of a 1:1:1 mixture of coconut oil and alpha linolenic acid and myristic acid;
b. 25 weight % carboxymethylcellulose
c. 30 weight % elastomer (KRATON®)
d. 15 weight % tackifier (FORAL®85)
EXAMPLE 7 is a representative composition of one aspect of the present invention.
a. 50.0 weight % of a 1:2:1 mixture of coconut oil and alpha linolenic and myristic acid;
b. 25 weight % carboxymethylcellulose
c. 15 weight % elastomer (KRATON®)
d. 10 weight % tackifier (FORAL®85)

EXAMPLE 8—CLINICAL EXAMPLE

The wound dressing composition of the present invention is effective in the management of:
i) Chronic and acute, moderate to heavy exudating, partial and full thickness wounds including superficial wounds
ii) 2nd degree burns
iii) Pressure ulcers, Stages II-IV As the present invention may be embodied in several forms without departing from the spirit or essential characteristics thereof, it will be understood the invention is no limited by the details of the foregoing description, unless otherwise specified, but rather should be construed broadly within its spirit and scope as defined in the appended claims, and therefore all changes and modifications that fall within the metes and bounds of the claims. Accordingly, the invention is defined by the appended claims wherein:

What is claimed:

1. An adhesive composition applicable to skin consisting of
   (i) coconut oil;
   (ii) one or more polymers from the group consisting of styrene isoprene styrene (SIS), styrene butadiene styrene (SBS), styrene ethylene-butylene styrene (SEBS), styrene-ethylene-styrene (SES), styrene-propylene-styrene (SPS), and ethylene vinyl acetate (EVA);
   (iii) mineral oil, and
   (iv) a tackifier.
2. An adhesive composition applicable to skin consisting of
   (i) coconut oil;
   (ii) one or more polymers from the group consisting of styrene isoprene styrene (SIS), styrene butadiene styrene (SBS), styrene ethylene-butylene styrene (SEBS), styrene-ethylene-styrene (SES), styrene-propylene-styrene (SPS), and ethylene vinyl acetate (EVA); and
(iii) a tackifier.

3. The adhesive composition of either of claim 1 or 2, wherein the tackifier is selected from the group consisting of natural rosin, modified rosin, glycerol ester of natural rosin, glycerol ester of modified rosin, pentaerythritol ester of natural rosin, pentaerythritol ester of modified rosin, phenolic-modified terpene resin, aliphatic petroleum hydrocarbon resin, and cycloaliphatic resin.

4. The adhesive composition of either of claim 1 or 2, wherein the ratio of polymer to the total amount of oil present in the composition ranges from about 1:1 to about 1:2 by weight.

\* \* \* \* \*